United States Patent [19]

Apostolatos et al.

[11] 4,118,332

[45] Oct. 3, 1978

[54] SYNERGISTIC ANTIBACTERIAL COMPOSITION CONTAINING MIXTURES OF CERTAIN HALOGENATED DIPHENYL ETHERS AND TRICHLOROCARBANILIDES

[75] Inventors: George Nikolas Apostolatos, New York, N.Y.; James Calvin Bohrer, East Brunswick; Jack Thomas Inamorato, Westfield, both of N.J.

[73] Assignee: Colgate-Palmolive Company, New York, N.Y.

[21] Appl. No.: 709,799

[22] Filed: Mar. 1, 1968

Related U.S. Application Data

[63] Continuation-in-part of Ser. No. 502,577, Oct. 22, 1965.

[51] Int. Cl.$^2$ .......................... C11D 3/48; C11D 9/50
[52] U.S. Cl. .................... 252/107; 252/106; 424/235; 424/322; 424/340
[58] Field of Search ............... 167/31, 30 C; 252/106, 252/107; 424/340, 235, 322

[56] References Cited

U.S. PATENT DOCUMENTS

| | | | |
|---|---|---|---|
| 2,818,390 | 12/1957 | Beaver | 167/31 |
| 3,134,711 | 5/1964 | Reller | 167/31 |
| 3,445,398 | 5/1969 | Jungermann et al. | 252/107 |
| 3,723,326 | 3/1973 | Cheng et al. | 252/107 |
| 3,956,489 | 5/1976 | Molnar | 424/233 |

FOREIGN PATENT DOCUMENTS

| | | | |
|---|---|---|---|
| 644,153 | 8/1964 | Belgium | 167/31 |
| 6,401,526 | 8/1964 | Netherlands | 167/31 |

*Primary Examiner*—P.E. Willis, Jr.
*Attorney, Agent, or Firm*—Norman Blumenkopf; Herbert S. Sylvester; Murray M. Grill

[57] ABSTRACT

Antibacterial compositions are provided comprising a polyhalogeno-hydroxydiphenyl ether and either a tribrominated salicylanilide or a trichlorocarbanilide in a weight ratio of 9:1 to 1:9; these compositions are particularly effective in combination with detergent materials.

18 Claims, No Drawings

SYNERGISTIC ANTIBACTERIAL COMPOSITION CONTAINING MIXTURES OF CERTAIN HALOGENATED DIPHENYL ETHERS AND TRICHLOROCARBANILIDES

This application is a continuation-in-part of application Ser. No. 502,577 filed Oct. 22, 1965.

This invention relates to antibacterial compositions. More particularly, this invention relates to antibacterial compositions which comprise in combination a diphenyl ether with halogenated salicylanilides or halogenated carbanilides, and to detergent compositions containing said antibacterial compositions as hereinafter described.

The demand for antibacterial compositions for use in the detergent and cosmetic field has risen tremendously in the last decade. Numerous detergent and soap compositions containing alleged antibacterial agents, or so-called antiperspirant or deodorant agents, are being commercially exploited as a means of restraining the organisms which generate odor from the human body by the decomposition of apocrine sweat. The desire for controlling axillary odor has predominated in the antibacterial detergent compositions presently on the market. In this regard, considerable research has been directed towards reducing the resident bacteria skin-flora which is instrumental in the generation of odor. It should be noted that such body odor is primarily generated by the decomposition of sebum and perspiration. Since this decomposition is initiated by the normal skin-flora, it follows that by reducing the skin-flora, i.e., the resident bacteria, these odors can be effectively reduced or even prevented. The skin-flora, however, do not merely contain the gram-positive bacteria which are instrumental in causing offensive odors but also contain gram-negative organisms. These latter organisms are often responsible for skin infections. Therefore, it is desirable to obtain a composition which will decrease both the gram-positive and gram-negative organisms inherent in the skin-flora, and thereby effect the reduction of both, the skin-flora which tend to cause offensive odors, and the gram-negative (and also gram-positive) skin-flora which causes local skin infections.

According to this invention, an antibacterial composition effective against both gram-positive and gram-negative bacteria comprises in combination, (1) a diphenyl ether compound having the formula:

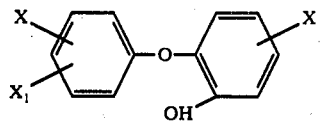

wherein X is a halogen, and $X_1$ is a member selected from the group consisting of hydrogen and a halogen; and (2) at least one compound selected from the group consisting of (A) a tribrominated salicylanilide of the general formula:

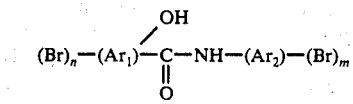

wherein $Ar_1$ and $Ar_2$ represent benzene rings; the OH group on $Ar_1$ is viewed the

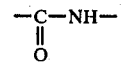

group; $n=1$ or 2; $m=1$ or 2 and $n+m=3$, and (B) a trichlorocarbanilide of the general formula:

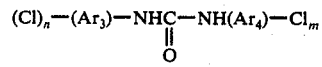

wherein $Ar_3$ and $Ar_4$ represent benzene rings and $n+m$ are 1 or 2 and $n+m=3$, the ratio of (1) to (2) suitably being from about 1:9 to about 9:1. It is to be understood that for the purposes of this invention, the material represented by (2) can also comprise a mixture of a tribromosalicylanilide and a trichlorocarbanilide.

Other substituents may be present in the benzene rings $Ar_1$, $Ar_2$, $Ar_3$ and $Ar_4$ such as alkyl, alkoxy (preferably lower alkyl and alkoxy of $C_1$ to $C_8$), and trifluoromethyl.

It has been found that combinations of the foregoing substances represented by compound (1) and (2) effect results in which the degree of antibacterial activity is greater than would be expected from the individual components taken independently. Moreover, it has been surprisingly found that the antibacterial compositions of the subject invention evidence not only an increase in bacteriostasis but also are highly substantive in their bacteriostatic effect. In this latter connection, it should be noted that bacteria, if merely inhibited, may be quickly reactivated by outside impulses such as moisture, temperature, and the like. This factor of reactivation is an especially important consideration for an antibacterial detergent composition intended to combat the aforesaid skin-flora. It is desirable, therefore, that an antibacterial agent employed in a detergent composition be more than just bacteriostatic or bacteriocidal, but that it be also substantive to the skin, i.e., that antibacterial activity will persist on the skin for extended periods of time after application thereto.

The diphenyl ether compounds employed in the practice of the subject invention are preferably either: 4,2',4'-trichloro-2-hydroxy diphenyl ether or 4,4'-dichloro-2-hydroxy diphenyl ether. Of the two, the trichloro compound has been found to be particularly effective. 4-4'-dichloro-2-hydroxy diphenyl ether may be suitably prepared by initially reacting 3-chloro-6-fluoro-1-nitrobenzene with the sodium salt of p-chlorophenol in a solution of ethyl alcohol heated to boiling. Thereafter the following precursor is obtained:

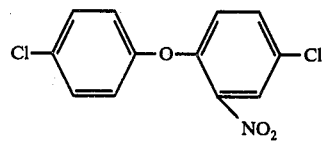

This compound is thereupon reduced by reaction with HCl and $NaNO_2$ and then introduced into water whereupon the hydroxy dichloro diphenyl ether is obtained. For the production of the trichloro compound, the sodium salt of 2,4-dichlorophenol can be used instead of the sodium salt of p-chlorophenol in the above reaction.

The second essential ingredient is the tribromosalicylanide or trichlorocarbanilide or mixtures thereof.

The preferred compounds are unsubstituted such as 3,5,4'-tribromosalicylanilide,
3,4',5-tribromosalicylanilide,
3,4,4'-trichlorocarbanilide, and
3,3',4-trichlorocarbanilide Illustratively, a combination of 3,4,4'-trichlorocarbanilide or 3,5,4'-tribromosalicylanilide with the aforesaid diphenyl ethers effects a synergism or potentiation which has been found to be particularly desirable in the practice of the subject invention. This latter effect is of importance since, as a consequence, lower proportions of each can be employed while still effecting the desired level of antibacterial activity. It is also important from the view-point of economics.

Both the salicylanilide and carbanilide components of the subject composition are known bacteriostats and have been heretofore employed in antibacterial compositions. Their effect, however, has been found to be greatly enhanced by combination with the aforesaid diphenyl ethers to form the compositions which comprise the subject invention.

In the practice of the subject invention, the ratio of the diphenyl ethers to either the salicylanilide or carbanilide components may suitably be from about 9:1 to about 1:9 and preferably from about 1:3 to about 3:1. Particularly preferable in order to effect optimum synergistic activity is a composition in which the proportion of the diphenyl ether to the salicylanilide or carbanilide is 1:1. In this regard a highly effective composition comprises about equal amounts of 4,2',4'-trichloro-2-hydroxy diphenyl ether, and 3,5,4'-tribromosalicylanilide. Optionally, a highly effective composition can also be obtained using substantially 100% trichlorocarbanilide in combination with equal parts of the diphenyl ether.

Another aspect of the subject invention comprises a surface active composition containing the antibacterial compositions disclosed above. In this connection, detergent compositions containing the aforedescribed antibacterial compositions are effective in reducing the skin-flora, both of the gram-positive and gram-negative type, when employed in ordinary washing procedures. As an illustration, the detergent compositions comprising a surface active compound and the antibacterial compositions of the subject invention are effective in reducing gram-positive bacteria such as *Staphylococcus aureus* and *Bacillus subtilis* and gram-negative bacteria such as *Escherichia coli*, *Staphylococcus aureus* being a principle agent in causing the aforesaid decomposition of the sebum and perspiration and thus offensive odor, and the latter gram-negative bacteria being an agent thought to be involved in skin irritations and other forms of infection.

In the practice of the subject invention, the term "surface active compound" suitably includes anionic, nonionic, cationic and amphoteric detergents and mixtures thereof.

Among the suitable anionic detergents are the water soluble soaps and sulfated or sulfonated synthetic detergents. In this regard, the soaps useful in the subject invention are generally the water-soluble salts of higher fatty acids (including rosin acids) which are derived usually from fats, oils and waxes of animal, vegetable or marine origin, e.g., tallow, coconut oil, tall oil, palm kernel oil soaps and the like. Particularly preferred soaps are the sodium and potassium salts of coco-tallow mixtures in ratios of 10–60 parts of the coco salts of 90–40 parts of the tallow salts.

With respect to the sulfonated synthetic detergents, it is preferred to employ a higher alkyl aryl sulfonate such as an alkyl benzene sulfonate detergent wherein the alkyl group has about 8 to 18 carbon atoms. Suitable examples are sodium decyl benzene sulfonate, sodium dodecyl and pentadecyl sulfonates wherein the dodecyl and pentadecyl groups are derived from a propylene polymer, and linear alkyl benzene sulfonates such as sodium keryl benzene sulfonate, sodium n-tridecyl benzene sulfonate, and sodium n-hexadecyl benzene sulfonate. Other suitable agents are the surface active water soluble salts of sulfated or sulfonated aliphatic compounds, preferably having 8 to 22 carbon atoms. Examples thereof are alkyl sulfonates and sulfuric acid esters of polyhydric alcohols incompletely esterified with higher fatty acids (e.g., sodium coconut oil monoglyceride monosulfate); the long-chain pure or mixed higher alkyl sulfates (e.g., sodium laury sulfate, coconut fatty alcohol sulfate); sulfates of the ethoxylated higher aliphatic alcohols such as ammonium lauryl alcohol triethoxamer sulfate; the higher fatty acid ethanolamide sulfates (e.g., sodium coconut fatty acid ethanolamide sulfate); the higher fatty acid amines of amino alkyl sulfonic acids (e.g., sodium lauric acid amide of taurine); the higher fatty acid esters of isethionic acid; and the like. These anionic surface active agents are used generally in the form of their water-soluble salts, such as the alkali metal (e.g., sodium, potassium), though other soluble salts such as ammonium, alkylolamine and alkaline earth metal salts may be used if desired, depending upon the particular detergent.

Other suitable anionic detergents include synthetic detergents having a carboxylate group, and particularly the higher fatty acid amides of aliphatic amino acid compounds. A typical example is the higher fatty acyl sarcosinates having about 10 to 18 carbons, usually 12-14 carbons, in the acyl radical, preferably the water-soluble salts of N-lauroyl or N-cocoyl sarcosine. Other materials are the higher fatty acid amides of polypeptide amino acids obtained by protein hydrolysis known as the Lamepons and Maypons. Other suitable detergents with carboxylate groups are various cationic and amphoteric detergents described hereinafter. Suitable ether-containing sulfates may be used also such as the alkylphenol polyglycol ether sulfates, e.g., lauryl phenol polyethyleneoxy sulfates, and alkyl polyglycol ether sulfates, e.g., lauryl ethyleneoxy sulfates, each containing about 10 to 18 carbons in said alkyl groups and usually averaging about 2 to 10 moles of ethylene oxide, usually 3-4 moles, per molecule.

Various nonionic agents may be employed also, such as the nonionic polyalkylene oxide condensates with an aliphatic or aromatic hydrophobic group. The hydrophobic organic group contains usually between at least 8 to 30 carbon atoms condensed with at least about 5 and usually up to 50 alkylene oxide groups. Examples are the polyethylene oxide condensates with alkyl phenols having 6 to 20 carbons in the alkyl group, such as Igepal CA and CO; the polyethylene oxide esters with higher fatty acids, such as tall oil acids or lauric acid condensed with about 16 to 20 ethylene oxide groups; the polyethylene oxide condensates with higher aliphatic alcohols, such as lauryl, myristyl, oleyl or stearyl alcohol with 6 to 30 moles ethylene oxide; the polyoxyethylene oxide condensates with higher fatty acid amides, such as coconut fatty acid amide containing about 10 to 50 moles ethylene oxide. The water-soluble polyoxyethylene condensates with hydrophobic polyoxypropylene glycols may be employed also. It is to be understood that the foregoing detergents are purely illustrative and that many other detergent materials may be also employed.

Cationic detergents wherein a quaternary nitrogen is part of an open chain or heterocyclic structure may also be used alone or in combination with other compatible detergents. Suitable salts are the chloride, bromide, acetate, sulfate, methosulfate and the like. Examples are lauroyl pyridinium bromide, N(lauroyl colamino formylmethyl) pyridinium chloride, cetyl trimethyl ammonium chloride, cetyl pyridinium chloride, stearyl or oleyl dimethylbenzyl ammonium chloride, stearyl amine acetate, stearyl dimethyl amine hydrochloride.

Other suitable surface active agents which can under certain conditions have a cationic nature and which may be used include the higher alkyl amine oxides such as aluryl dimethyl amine oxide. In place of the lauryl radical, other long chain alkyl radicals, preferably having 10 to 18 carbon atoms, may be used also. In place of either or both methyl radicals, there may be other lower alkyl or hydroxyalkyl radicals such as having two carbon atoms each. Suitable examples include a mixture of higher alkyl dimethyl amine oxides having essentially about 12–14 carbons in the higher alkyl groups.

Any of the usual amphoteric (ampholytic) detersive materials may also be employed in the compositions of the present invention. Among those are fatty or higher alkyl imidazolines, such as 1-coco-5-hydroxyethyl-5 carboxymethyl imidazoline known as Miranol $C^M$; and the higher alkyl beta-alanines such as dodecyl beta-alanine known as Deriphats, said materials having usually an alkyl group of 10 to 18 carbons and the carboxylate group being in the form of the water-soluble salt. Further examples are the disodium salt of 1-lauryl-cycloimidium-2-ethoxy-ethionic acid and its corresponding 2-lauryl sulfate derivative.

In the embodiment represented by the antibacterial detergent composition, the mixture of diphenyl ether with salicylanilide or carbanilide should suitably be included in amounts of from about 0.01 percent to about 5 percent by weight of the detergent composition and preferably from about 1 to about 2 percent. A particularly excellent product has been found to be a soap bar comprising milled and plodded soap chips prepared from 20% sodium coco soap and 80% sodium tallow soap and containing 0.5 to 1.5 percent by weight of 4,2′,4′-trichloro-2-hydroxy diphenyl ether and 0.5 to 1.5 percent by weight of 3,5,4′-tribromosalicylanilide.

The antibacterial composition of this invention can be included in detergent compositions such as soap bars, spray-dried and granulated solid compositions, synthetic non-soap detergent bars and combination soap-synthetic detergent bars and liquid detergent compositions, and the like, in any suitable manner known to the art. They can also be included in presurgical scrubbing compositions which are widely employed in the medical field. The latter detergent compositions usually comprise a liquid composition containing a detergent such as a potassium soap, a triethanolamine lauryl sulfate, a sodium lauryl ether sulfate and the like. It is to be understood that various other ingredients can be included in addition to the antibacterial composition and the detergent per se, such as inorganic and organic water soluble builder salts. Among the most common of these compounds are the water soluble salts, usually alkali metal or ammonium salts, of sulfuric, phosphoric, silicic, carbonic, boric, nitrilotriacetic, ethylenediamine tetra acetic, hydrochloric, and polyphosphonic acids, and derivatives thereof. Of the builder salts, the polyphosphates and aminocarboxylates are of greatest utility and applicability, but sodium and potassium sulfate, sodium carbonate, sodium silicate, sodium bicarbonate, sodium perborate, borax, sodium chloride, sodium phosphates such as disodium hydrogen phosphate, to name only a few, also exercise desirable building activity.

Various other adjuvant ingredients may be added as is found desirable including compatible perfumes, coloring materials, corrosion or tarnish inhibitors, fluorescent brighteners, thickeners, solvents, lubricants (to promote flowability), foam enhancers and stabilizers, waxes, colloidal materials such as bentonite, and so forth. These adjuvants are usually present in minor amount, rarely exceeding 20% and often totaling about 5% and are usually incorporated to improve specific esthetic or performance characteristics. The amount of solvent may be as much as half the aqueous solvent of a liquid detergent. If desired, the antibacterial composition may be initially dissolved in a suitable solvent before introduction into a detergent system.

In the formulation of the preferred soap bar of the subject invention, a suitable procedure comprises mixing soap chips with the antibacterial composition, either in granular or liquid (i.e., dissolved in a solvent) form, plus such adjuvants as are desired, introducing the mixture thus formed into a soap milling apparatus whereby uniform mixing of all ingredients takes place, and thereafter plodding and pressing the mixture to the desired shape.

The following examples will illustrate further the scope and practice of this invention. However, it is to be understood that they are purely by way of illustration and are not to be considered in any way as a limitation of the scope of the compositions forming the subject invention. Except as otherwise indicated, the proportions and percentages employed are by weight.

In the Examples, 3,5,4′-tribromosalicylanilide will be represented by the designation "TBS," 3′,4′,5-tribromosalicylanilide by the designation "TBS-I" while 3,4,4′-trichlorocarbanilide will be represented by the designation "TCC." In addition, the following test procedures are among those employed to determine the efficacy of the compositions of the subject invention.

A. STREAK TEST

This test comprises adding a bacteriostat-containing detergent solution to a pre-determined amount of warm tryptone glucose extract agar, in amounts sufficient to obtain the desired concentration of bacteriostat in the agar fluid. This fluid mixture is then poured into a Petri dish and allowed to harden. A 4mm standard loop of an overnight broth culture of *Staphylococcus aureus*, FDA strain 209, is then added to the Petri dish and uniformly distributed over the surface of the hardened agar. The Petri dish is then incubated for 48 hours at 37° C. and the bacterial growth is rated as follows:

0 = no growth
+ = slight growth
+2 = medium growth

+3 = heavy growth

B. TIME KILL TEST

This test was developed by Cade and Halverson (Cade, A.R., and Halverson, H.O., SOAP, Vol. 10, #9, Page 25.) This test comprises the steps of preparing an aliquot of a detergent solution from a soap bar or other type detergent composition containing the desired amount of bacteriostatic composition. This solution is then added to FDA nutrient broth in amounts such as to obtain the desired concentration of bacteriostat in the broth. The broth-detergent-bacteriostat fluid is then heated at 37° C. in a water bath and innoculated with a 0.1 ml. solution of a standard overnight culture of *Staphylococcus aureus* (FDA 209) (or other bacteria being employed). After 10 minutes of incubation, an aliquot of mixture is removed and diluted in 0.1% peptone water diluent and mixed with a certain amount of warm trypticase soy agar. This final mixture is then poured into a Petri dish and after solidification of the agar, the Petri dish is incubated at 37° C. for 24 hours. In this period of incubation, surviving bacteria cells mature into bacteria colonies. These are then counted in a reqular Quebac colony counter. The resulting figure represents the number of bacteria cells, which survived a ten minute exposure to the antibacterial composition.

C. SERIAL DILUTION TEST

In order to determine the minimum amount of the antibacterial agent needed to inhibit the bacteria growth the Serial Dilution test is employed. In this test a solution of the antibacterial composition is prepared using dimethyl sulfoxide as a suitable solvent. An aliquot of this solution is added to the first of a series of tubes containing trypticase soy broth, thus resulting in a fluid mixture of broth with a certain concentration of antibacterial composition. This concentration is thus reduced serially by removing an aliquot from the first tube and adding it to the second tube and so on to obtain a series of solutions with decreasing amounts of antibacterial composition. The tubes are innoculated with an overnight culture of the test organism and incubated for 48 hours at 37° C. The minimum inhibitory concentration is recorded as the lowest concentration at which no visible growth occurred.

If desired, other tests such as, for example, the so-called "Cade" handwashing test, direct axillary bacterial count, and the like may be employed as the test procedures.

EXAMPLE I

Antibacterial compositions according to the subject invention are prepared by intimately mixing the ingredients listed in Table I below, in the proportions given. The numbers represent the ratios of ingredients to each other. Thus for example, one part of the 4,2',4'-trichloro-2-hydroxy diphenyl ether is combined with an equal portion, i.e., one part of TBS, in column A. In like manner, the remaining columns represent the ratio of ingredients in parts or fractions of parts to each other to form illustrative inventive compositions.

TABLE I

| | A | B | C | D | E | F | G | H | I | J | K | L | M | N | O | P | Q | R | S | T | U | V | W | X | Y | Z | AA |
|---|---|---|---|---|---|---|---|---|---|---|---|---|---|---|---|---|---|---|---|---|---|---|---|---|---|---|---|
| 4,2',4'-trichloro 2-hydroxy diphenyl ether | 1.0 | 1.0 | 1.0 | 1.0 | | | | | 1.5 | 1.5 | 1.5 | 1.5 | | | | 0.67 | | 0.67 | 0.5 | 0.5 | 0.5 | 0.5 | 0.2 | 0.2 | 0.2 | 1.8 | 1.8 |
| 4,4'-dichloro-2-hydroxy diphenyl ether | | | | | 1.0 | 1.0 | 1.0 | 1.0 | | | | | 1.5 | 1.5 | 1.5 | | 0.67 | | | | | | | | | | |
| TBS+DBS* (85:15) | 1.0 | | | | 1.0 | | | | 0.5 | | | | 0.5 | | | 0.67 | 0.67 | | 1.5 | | | | 1.8 | | | 0.2 | |
| TCC | | 1.0 | | | | 1.0 | | | | 0.5 | | | | 0.5 | | 0.67 | 0.67 | 0.67 | 1.5 | | | | 1.8 | | | | 0.2 |
| TBS | | | 1.0 | | | | 1.0 | | | | 0.5 | | | | 0.5 | | 0.67 | | | 1.5 | | | | 1.8 | | | 0.2 |
| TBS-I | | | | 1.0 | | | | 1.0 | | | | 0.5 | | | | | | | | | 1.5 | | | | | | |

*DBS is 3,5-dibromosalicylanilide which is present in the TBS to the extent of 15% by weight.

The above compositions are found to exhibit marked bacteriostatic properties against both gram-negative and gram-positive bacteria such as Escherichia Coli and Staphylococcus Aureus.

EXAMPLE II

A series of milled and plodded soap bars are prepared in which the soap content is 94.32%, which percentage comprises 20% sodium soap derived from coconut oil and 80% sodium soap derived from tallow. Each of the soap bars contain 2.0% by weight of an active ingredient, as indicated below in Table 2. It is to be noted that bars "K" and "O" are "control" bars in which the active ingredient is exclusively either 4,2',4'-trichloro-2-hydroxy diphenyl ether or TBS. Bars "L," "M," and "N" represent bars according to the subject invention in which the active ingredient is an antibacterial composition of the subject invention, in varying proportions, as indicated.

The remainder of Table 2 discloses the results obtained using the "streak test" previously defined. The test procedure employed is as follows:

Solutions of the aforesaid soap bar containing an antibacterial composition are prepared, said solutions being of varying concentration so that when added to nutrient tryptone glucose extract agar, the following soap concentrations are obtained in the agar: 8, 16 and 32 parts per million, respectively. In each of these three fluid mixtures, the antibacterial composition is present in amounts of 0.16, 0.32 and 0.64 parts per million, respectively. Each of the fluid mixture is separately poured into a different Petri dish and allowed to harden. A 4mm. standard loop of an overnight broth culture of Staphylococcus Aureus is then added to the Petri dish.

The contents of the Petri dish are then incubated for 48 hours at 37° C. and bacterial growth is rated according to the legend indicated in the following table.

TABLE 2

| ppms of Soap | 32 | 16 | 8 |
|---|---|---|---|
| ppms of Bacteriostat | 0.64 | 0.32 | 0.16 |
| Bar Active Content | Growth Indicated | | |
| K  2.0% 4,2',4'-trichloro-2-hydroxy diphenyl ether | + | + | + |
| L  1.5% 4,2',4'-trichloro-2-hydroxy diphenyl ether + 0.5% TBS* | 0 | 0 | + |
| M  1.0% 4,2',4'-trichloro-2-hydroxy diphenyl ether + 1.0% TBS* | 0 | 0 | + |
| N  0.5% 4,2',4'-trichloro-2-hydroxy diphenyl ether + 1.5% TBS* | 0 | + | + |
| O  2.0% TBS* | + | +3 | +3 |

Legend:
0 = No growth
+ = Slight growth
+2 = Medium growth
+3 = Heavy growth
* This TBS contains 15% 3,5-dibromosalicylanilide.

EXAMPLE III

Milled and plodded soap bars in which the soap content is 94.32% which percentage comprises a mixture of 20% sodium soap derived from coconut oil and 80% sodium soap derived from tallow are prepared. In each of said bars there is incorporated 2.0% by weight of the active ingredients according to the subject invention in varying proportions, as follows:

| Bar | Percentage of 4,2',4'-trichloro-2-hydroxy diphenyl ether | Percentage of TBS |
|---|---|---|
| 1 | 90 | 10 |
| 2 | 80 | 20 |
| 3 | 70 | 30 |
| 4 | 60 | 40 |
| 5 | 50 | 50 |
| 6 | 40 | 60 |
| 7 | 30 | 70 |
| 8 | 20 | 80 |
| 9 | 10 | 90 |

The above indicated bars are found to be bacteriostatic and to inhibit the growth of both *Staphylococcus aureus*, *Bacillus subtilis* and *Escherichia coli*, using the "time kill test" or "serial dilution test" previously described.

EXAMPLE IV

Six compositions are prepared as indicated in the table below. By means of the "serial dilution test," the minimum amount of antibacterial agent needed to inhibit the bacterial growth of a gram-positive bacteria, *Bacillus subtilis*, is determined. The test procedure is as follows:

Into a row of 10 test tubes, each of which is 13 × 100 mm., there is dispensed trypticase soy broth as follows:

In the first tube there is dispensed 3.6cc of the broth. In tubes 2 through 10, 2.0cc of the soy broth is dispensed. Thereafter, a 0.1% solution of each of the active ingredients indicated below is prepared by dilution of the same in dimethyl sulfoxide; 0.4cc of this solution is then pipetted into the first test tube with a 2.0mm Bicknell pipette; the content of each test tube is then mixed thoroughly. 2cc are extracted from the first test tube and inserted into the second tube. This procedure is then repeated on through the remaining tubes. Each of the tubes is then innoculated with 0.1cc of an overnight culture of *Bacillus subtilis*, and incubated for 48 hours at 37° C. The minimum inhibitory concentration is then recorded as the lowest concentration in micrograms/milliliter in which no visual growth occurred.

TABLE 3

| Solution Containing .1% Active Ingredient (a), (b), (c), (d) & (e) | Minimum Inhibitory Concentration in Micrograms/Ml |
|---|---|
| (a) 4,2',4'-trichloro-2-hydroxy diphenyl ether | 1.56 |
| (b) TBS* | 1.56 |
| (c) TCC | 3.12 |
| (d) 4,2',4'-trichloro-2-hydroxy diphenyl ether +TBS* | .39 + .39 |
| (e) 4,2',4'-trichloro-2-hydroxy diphenyl ether + TCC | .39 + .39 |

EXAMPLE V

| Components | Percentage |
|---|---|
| Lauryl alcohol triethoxamer ammonium sulfate | 14.00 |
| Ethanol | 6.00 |
| Lauric/Myristic (70:30) Monoethanolamide | 6.00 |
| Sodium alkyl benzene sulfonate in which the alkyl group is a mixture of $C_{10}$–$C_{13}$ | 18.30 |
| Sodium xylene sulfonate | 7.00 |
| Water | 47.20 |
| Sodium sufate | 1.00 |
| 4,2',4'-trichloro-2-hydroxy diphenyl ether | 0.05 |
| TBS | 0.05 |
| Adjuvants (color, perfume, etc.) | 0.40 |
| Total | 100.00 |

*This TBS contains 15% 3,5-dibromosalicylanilide.

The above liquid detergent evidences high bacteriostatic activity. The active ingredients, i.e., the diphenyl ether and TBS are initially dissolved in a 95% alcoholic solution including approximately 150 ppm triethanolamine, prior to addition to the liquid formulation.

EXAMPLE VI

| Components | Percentage |
|---|---|
| Sodium linear tridecylbenzenesulfonate | 21.00 |
| Sodium carboxy methyl cellulose | 0.40 |
| Polyvinyl alcohol | 0.20 |
| Borax decahydrate | 1.00 |
| Sodium silicate | 7.00 |
| Sodium sulfate | 25.80 |
| Pentasodium tripolyphosphate | 27.00 |
| Tetrasodium pyrophosphate | 7.00 |
| 4,2',4'-trichloro-2-hydroxy diphenyl ether | 0.05 |
| TBS | 0.05 |
| Adjuvants (Brighteners, Stabilizers, Perfume, etc.) | 2.00 |
| Water | 8.50 |
| Total | 100.00 |

The above heavy duty detergent composition is prepared by spray-drying a crutcher mix slurry of the above ingredients, minus the diphenyl ether and TBS ingredients. A 3% solution of the spray-dried mixture is then prepared. The active components are initially dissolved in a 95% alcoholic solution including approximately 150 ppm triethanolamine, and are then added to the 3% solution, previously prepared, with stirring. This composition evidences high bacteriostatic activity.

EXAMPLE VII

| Components | Percentage |
|---|---|
| Ethoxylated higher alcohol having 14–18 carbon atoms in the higher alkyl group and about 9.5 moles of ethylene oxide | 9.00 |
| Sodium carboxy methyl cellulose | 0.30 |
| Sodium silicate | 3.00 |
| Polyvinyl alcohol | 0.13 |
| Pentasodium tripolyphosphate | 27.00 |
| Tetrasodium pyrophosphate | 7.00 |
| Sodium sulfate | 44.60 |
| 4,2',4'-trichloro-2-hydroxy diphenyl ether | 0.04 |
| TBS | 0.04 |
| Water | 8.50 |
| Adjuvants (perfume, brighteners, stabilizers) | balance |
| Total | 100.00 |

The above heavy duty detergent is prepared by spray-drying a crutcher mix slurry of the above composition, minus the diphenyl ether and TBS ingredients. A 3% solution of the spray-dried mixture is then prepared. The active components are initially dissolved in a 95% alcoholic solution including approximately 150 ppm triethanolamine, and are then added to the 3% solution, previously prepared, with stirring. This composition evidences high bacteriostatic activity.

EXAMPLE VIII

| Components | Percentage |
|---|---|
| Potassium xylene sulfonate | 9.92 |
| Sodium tridecylbenzenesulfonate | 8.76 |
| Alcohol triethoxamer sodium sulfate in which the alkyl group of the alcohol is a mixture of $C_{12}$–$C_{14\ atoms}$ | 5.40 |
| Sodium sulfate | 1.48 |
| Tetrapotassium pyrophosphate | 15.00 |
| Lauric/Myristic isopropanolamide | 1.00 |
| Lauric/Myristic diethanolamide | 1.00 |
| Castor wax | 0.60 |
| Polyvinyl alcohol | 0.25 |
| 4,4'-dichloro-2-hydroxyl diphenyl ether | 0.06 |
| TCC | 0.06 |
| Water | 54.09 |
| Adjuvants (perfume, brighteners, etc.) | balance |
| Total | 100.00 |

The heavy-duty liquid detergent of the above formula is made by addition of powdered TCC and diphenyl ether, in the amounts indicated, to a mixture of the rest of the ingredients of the above formulation. This composition evidences high bacteriostatic activity.

EXAMPLE IX

| Components | Percentage |
|---|---|
| Triethanolammonium lauryl sulfate | 16.00 |
| Sodium lauryl ether sulfate | 10.00 |
| Mineral oil | 2.00 |
| Isopropyl myristate | 1.00 |
| Ethoxylated lanolin (16 moles ethylene oxide) | 3.00 |
| Lauric/Myristate diethanolamide | 1.50 |
| Diethyleneglycol monoethyl ether | 3.00 |
| 4,2',4'-trichloro-2-hydroxy diphenyl ether | 1.00 |
| TBS | 1.00 |
| Hydroxypropyl methylcellulose | 0.83 |
| Deionized water | 58.22 |
| Adjuvants (perfume, color) | 2.45 |
| Total | 100.00 |

The above composition is a surgical-scrubbing composition which exhibits high bacteriostatic action against both gram-positive and gram-negative bacteria.

EXAMPLE X

Synthetic detergent bar chips having the formula appearing below are prepared.

| Components | Percentage |
|---|---|
| Sodium tallow alcohol sulfate | 12.50 |
| Sodium hydrogenated coco-monoglyceride sulfate | 53.40 |
| Sodium chloride | 5.10 |
| Sodium sulfate | 6.50 |
| $C_{16}$–$C_{18}$ fatty alcohol mixture | 13.00 |
| Adjuvants | 8.00 |
| Water | balance |
| Total | 100.00 |

To 50 grams of the synthetic detergent bar chips above there is added 0.25 grams of powdered 4,4'-dichloro-2-hydroxy diphenyl ether and 0.25 grams of powdered TCC. To another 50 gram batch of said chips there is added 0.25 grams powdered 4,4'-dichloro-2-hydroxy diphenyl ether and 0.25 grams of powdered TBS.

Each 50 grams batch is then mixed thoroughly and milled and pressed to form synthetic detergent bars containing an antibacterial composition of the subject invention. Said bars exhibited marked bacteriostatic activity.

EXAMPLE XI

In like manner as in Example X, a combination soap, synthetic non-soap detergent "combar" is prepared having the following formulation:

| Components | Percentage |
|---|---|
| Soap solids prepared from a mixture of 15 parts coconut oil and 85 parts tallow | 76.50 |
| Sodium salt of alpha-sulfonated methyl ester of tallow fatty acids | 12.60 |
| Sodium sulfate | 0.90 |
| 4,4'-dichloro-2-hydroxy diphenyl ether | 0.50 |
| TCC | 0.50 |
| Water | 9.00 |
| Total | 100.00 |

This bar also exhibited high bacteriostatic activity.

EXAMPLE XII

A series of milled and plodded soap bars are prepared incorporating various concentrations of a 1:1 mixture of 4,2',4'-trichloro-2-hydroxy diphenyl ether and TBS. The soap employed is a combination of 20 percent sodium coco-soap and 80 percent sodium tallow soap, the total soap composition of the bar being 94 percent, the remainder being the percentage of antibacterial composition plus adjuvants.

In the soap bars, the percentages of antibacterial composition of the subject invention are varied from 0.1 percent by weight to 5 percent by weight. A pronounced bacteriostatic effect is obtained with each of the bars, with those bars in which the antibacterial composition is present in the range of 0.5 percent to 2 percent by weight, being the most effective.

EXAMPLE XIII

Example V is repeated employing in place of the alkyl benzene sulfonate an equal weight of sodium n-hexadecane sulfonate. Comparable results are obtained.

EXAMPLE XIV

Example VI is repeated, instead of benzene sulfonate there is used an equal weight of a sodium n-olefin sulfonate wherein the average carbon chain length of the olefin is $C_{12.5}$.

EXAMPLE XV

The outstanding efficacy of the compositions of this invention is demonstrated in the following modified Cade hand washing test. The purpose of this test is to show the effect of the antibacterial components under actual use conditions.

The general experimental details of the test are as follows: A panel of 20 persons, both male and female is selected and for two weeks each person uses a control bar of soap exclusively, and after the two week period each panel member is then given a supervised hand washing test and the wash water is evaluated to establish the panelist's normal bacterial population. In the tests a "Bactronic Colony Counter, Model C-110 is used." Under careful further supervision hand washing tests are conducted using soap bars similar in composition to those used in the initial test period, but containing in one group of tests 2% 4,2′,4′-trichloro-2-hydroxy diphenyl ether; in the second group, 2% 3,5,4′-tribromosalicylanilide and in the third group, 1% of each of the aforementioned compounds. The test bars are used for 10 days and then regular soap without the antibacterial additives for an additional 7 days. The results are as follows: The average reduction in bacterial population at the end of the fourth day employing the soap bars containing 2% tribromosalicylanilide is 79.5% reduction; and for seven days, 76.9%; and after 10 days, 85.4%. After four days back on regular soap, the value is 64.9% and after 7 days 38.9%. With the soap bars containing diphenyl ether, the corresponding reductions are 47.6% after four days; 65.8% after seven days; 67.4% after ten days, and when back to regular soap 56.4% after four days and 44.7% after seven days. With the soap containing 1% of each of the compounds, the results are after 4 days use, a reduction of 92.0%; after seven days 96.1% and after ten days 94.7%. Returning to regular soap after four days, the reduction is 65.9% and after seven days 50.6%.

The superiority of the 1:1 mixture is clearly evidenced by the above data.

EXAMPLE XVI

In order to further demonstrate the superior properties of the antibacterial compositions of this invention over the range of 1:9 to 9:1 on a weight basis, halo tests were carried out in the following manner: Culture plates are prepared containing 20cc. of nutrient agar in the Petri dish. There is then added 5cc. of seeded agar (prepared by the addition of 2ml. of Staphylococcus Aureus (FDA 209) organism grown in an overnight broth culture, and then added to 100ml. of melted, cool seed agar.) One-half inch discs (6.6mm) of filter paper (specifically available for biological assay work) are dipped in an alcoholic solution of the selected antibacterial composition and laid on the agar in the dish. The assembly is incubated overnight at 35° C. and the halos indicating the region of inhibition are measured using a Fisher-Lilly Zone Reader. A plurality of runs are made at various concentrations and ratios of the antibacterial materials with the following results: At a concentration of 0.005% of the 4,2′4′-trichloro-2-hydroxy diphenyl ether, the halo is 12.2mm. At the same concentration 3,5,4′-tribromosalicylanilide gives no halo, or in other words, there is no inhibiting action against the organism. At a concentration of 0.0045% the diphenyl ether compound gives a halo of 12.0mm; at 0.0035% the halo is 10.0mm; at 0.0025% the halo is somewhat less than 7.9mm and 0.0015% there is no halo.

The following mixtures of diphenyl ether and the salicylanilide are tested with the following results:
1. 0.0045% diphenyl ether + 0.005% tribromo salicylanilide gives a halo of 14.0mm.
2. 0.0035% diphenyl ether + 0.0015% of the tribromosalicylanilide gives a halo of 13.4mm.
3. 0.0025% of each gives a halo of 13.1mm.
4. 0.0015% diphenyl ether and 0.0035% tribromosalicylanilide gives a halo of 13.4mm.
5. 0.0005% diphenyl ether and 0.045% tribromosalicylanilide gives a halo of 9.3mm.

The above data clearly demonstrates the remarkable antibacterial activity of the mixtures within the range of 1:9 to 9:1 on a weight basis which is superior to the diphenyl ether alone at equal diphenyl ether concentrations and patently superior to the tribromosalicylanilide which has no inhibitory activity at the highest concentration used alone.

Although the present invention has been described with reference to particular embodiments and examples, it will be apparent to those skilled in the art that changes and modifications can be made without departing from the principles the true spirit of the invention. It is also to be understood that the term "detergent compositions" envisions a wide range of compositions including shampoos and the like, and that the antibacterial compositions of this invention can be included in many other vehicles apart from "detergent compositions," such as facial creams, after-shaving lotions, and the like.

What is claimed is:

1. An antibacterial composition effective against both gram-positive and gram-negative bacteria comprising in combination (1) a diphenyl ether compound having the formula

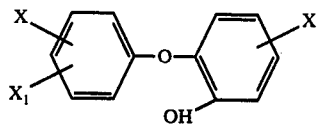

wherein X is a halogen and $X_1$ is a member selected from the group consisting of hydrogen and halogen; and (1) at least one compound selected from the group consisting of 3,4,4′-trichlorocarbanilide - and 3,3′4-trichlorocarbanilides the ratio of (1) to (2) being about 1:3 to 3:1.

2. A composition as defined in claim 1 wherein the diphenyl ether compound is polychlorinated.

3. A composition as defined in claim 2 wherein the diphenyl ether is 4,2′,4′-trichloro-2-hydroxy diphenyl ether.

4. A composition as defined in claim 2 wherein the diphenyl ether is 4,4′-dichloro-2-hydroxy diphenyl ether.

5. A composition as defined in claim 1 wherein the ratio of (1) to (2) is about 1:1.

6. A composition as defined in claim 3 wherein compound (2) is 3,4,4'-trichlorocarbanilide.

7. A composition as defined in claim 6 which comprises equal parts by weight of (1) and (2).

8. A composition as defined in claim 6 wherein the ratio of component (1) to (2) is about 1:3.

9. An antibacterial detergent composition effective against both gram-negative and gram-positive baterial comprising a detergent selected from the group consisting of soaps and non-soap synthetic anionic, nonionic, cationic and amphoteric detergents and from about 0.01% to about 5% by weight of a mixture of (1) of diphenyl ether compound having the formula

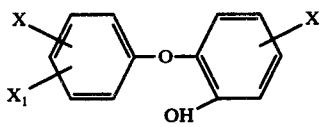

wherein X is a halogen and $X_1$ is a member selected from the group consisting of hydrogen and halogen; and (2) at least one compound selected from the group consisting of 3,4,4' trichlorocarbanilide - and 3,3'4-trichlorocarbanilide the ratio of (1) to (2) being about 1:3 to 3:1.

10. A composition as defined in claim 9 wherein the diphenyl ether compound (1) is 4,2',4' trichloro - 2-hydroxy diphenyl ether and compound (2) is 3,4,4' trichlorocarbanilide.

11. A composition as defined in claim 10 wherein the detergent is soap.

12. A composition as defined in claim 8 wherein the detergent is a coco-tallow soap.

13. A composition as defined in claim 9, wherein the detergent is an alkyl benzene sulfonate.

14. An antibacterial composition effective against both gram-negative and gram-positive bacteria comprising a synthetic, non-soap detergent selected from the group consisting of anionic, nonionic, cationic and amphoteric detergents, and from about 0.01% to about 5% by weight of a mixture of (1) a diphenyl ether compound having the formula:

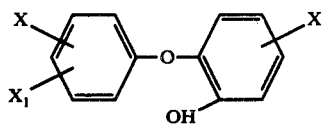

wherein X is a halogen and $X_1$ is a member selected from the group consisting of hydrogen and halogen; and (2) at least one compound selected from the group consisting of 3,4,4' trichlorocarbanilide - and 3,3',4-trichlorocarbanilide the ratio of (1) to (2) being about 1:9 to about 9:1.

15. An antibacterial composition as defined in claim 14 wherein the diphenyl ether compound (1) is 4,2,4' trichloro-2-hydroxy diphenyl ether and compound (2) is 3,4,4' trichlorocarbanilide.

16. A composition as defined in claim 15 wherein said detergent is an anionic synthetic detergent.

17. A composition as defined in claim 15 wherein said detergent is a nonionic synthetic detergent.

18. A composition as defined in claim 11 wherein the ratio of component (1) to (2) is 1:3.

* * * * *